(12) United States Patent
Boese et al.

(10) Patent No.: US 8,511,316 B2
(45) Date of Patent: Aug. 20, 2013

(54) INTERVENTIONAL INSTRUMENT WITH MARKING ELEMENT

(75) Inventors: Jan Boese, Eckental (DE); Norbert Rahn, Forchheim (DE); Bernhard Sandkamp, Erlangen (DE)

(73) Assignee: Siemens Aktiengesellschaft, München (DE)

( * ) Notice: Subject to any disclaimer, the term of this patent is extended or adjusted under 35 U.S.C. 154(b) by 1411 days.

(21) Appl. No.: 11/480,192

(22) Filed: Jun. 30, 2006

(65) Prior Publication Data

US 2007/0004981 A1 Jan. 4, 2007

(30) Foreign Application Priority Data

Jun. 30, 2005 (DE) .................. 10 2005 030 607

(51) Int. Cl.
*A61B 19/00* (2006.01)
(52) U.S. Cl.
USPC ............................................. 128/897
(58) Field of Classification Search
USPC ......................................... 128/897; 600/585
See application file for complete search history.

(56) References Cited

U.S. PATENT DOCUMENTS

| | | | |
|---|---|---|---|
| 4,279,252 A * | 7/1981 | Martin | 600/435 |
| 5,084,022 A * | 1/1992 | Claude | 604/164.13 |
| 5,103,804 A * | 4/1992 | Abele et al. | 600/116 |
| 5,156,151 A * | 10/1992 | Imran | 600/375 |
| 5,253,653 A * | 10/1993 | Daigle et al. | 600/585 |
| 5,479,938 A | 1/1996 | Weier | |
| 5,759,174 A * | 6/1998 | Fischell et al. | 604/103.1 |
| 6,285,903 B1 * | 9/2001 | Rosenthal et al. | 600/433 |
| 6,289,235 B1 * | 9/2001 | Webber et al. | 600/426 |
| 6,359,960 B1 * | 3/2002 | Wahl et al. | 378/20 |
| 6,473,488 B2 * | 10/2002 | Menhardt | 378/62 |
| 7,303,798 B2 * | 12/2007 | Bavaro et al. | 428/36.9 |
| 2002/0013540 A1 * | 1/2002 | Jacobsen et al. | 600/585 |
| 2002/0095205 A1 * | 7/2002 | Edwin et al. | 623/1.13 |
| 2004/0111044 A1 * | 6/2004 | Davis et al. | 600/585 |

FOREIGN PATENT DOCUMENTS

| | | |
|---|---|---|
| DE | 102 43 261 A1 | 3/2004 |
| DE | 102 55 030 A1 | 6/2004 |
| EP | 1 324 799 B1 | 7/2003 |
| GB | 2 355 797 A | 5/2001 |
| WO | WO 0130254 A1 * | 5/2001 |

* cited by examiner

*Primary Examiner* — Charles A Marmor, II
*Assistant Examiner* — Catherine E Burk

(57) ABSTRACT

To make interventional instruments such as catheters more easily identifiable in X-ray images, the catheters are provided with marking elements which can be recognized in the X-ray image. Examples of marking elements are sphere-shaped and ring-shaped marking elements, the ring-shaped marking elements being able to identify the catheters in the manner of a barcode and so being able to make different catheters distinguishable from one another in the X-ray image.

14 Claims, 2 Drawing Sheets

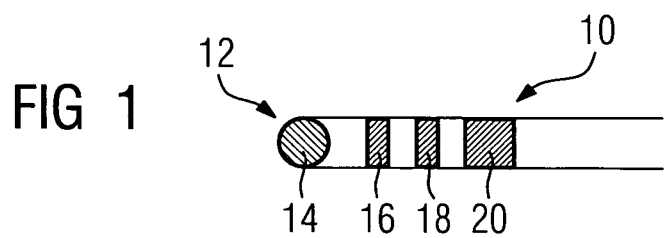
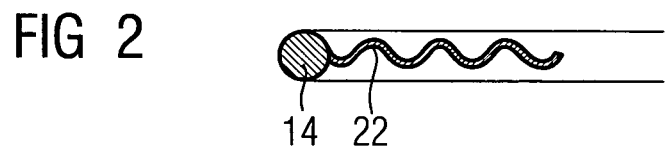
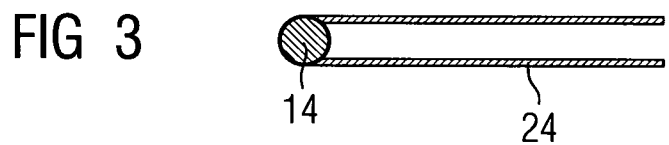
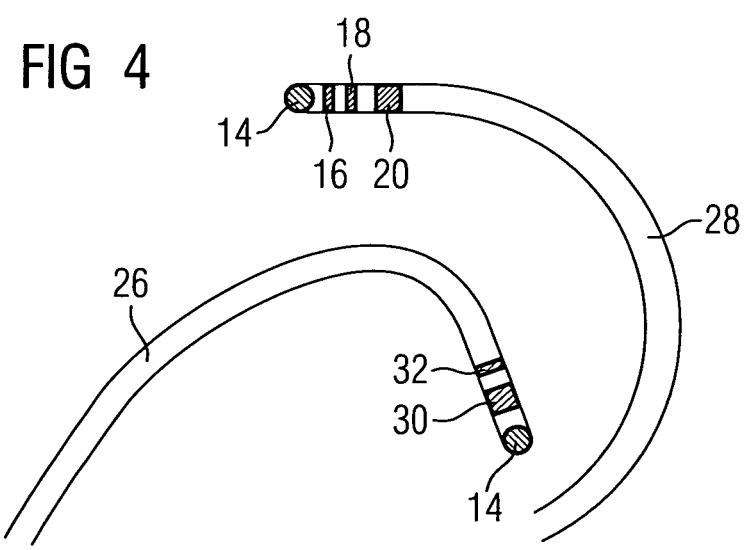

US 8,511,316 B2

INTERVENTIONAL INSTRUMENT WITH MARKING ELEMENT

CROSS REFERENCE TO RELATED APPLICATIONS

This application claims priority of German application No. 10 2005 030 607.1 filed Jun. 30, 2005, which is incorporated by reference herein in its entirety.

FIELD OF THE INVENTION

The present invention relates to an interventional instrument such as, for example, a catheter, a guide wire or a sheath. In electrophysiological treatments of a patient, for example, catheters are advanced as far as into the area of the patient's heart. This is usually performed under X-ray monitoring and control. In such situations a plurality of catheters may also be used depending on the type of treatment. During a catheter ablation procedure, for example, one catheter is used for the ablation while measurements are taken by means of a further catheter.

BACKGROUND OF THE INVENTION

The catheters that are used simultaneously may sometimes be difficult to differentiate from one another because they resemble one another in the X-ray image. This makes placement of the catheters more difficult.

For the electrophysiologist it is at best possible to track a catheter guided, i.e. moved, by him or her. If the catheters are stationary, the identification can be difficult. With automated detection methods it may in principle be possible to recognize a catheter in an X-ray image, although until now it has not been possible to identify catheters individually.

SUMMARY OF THE INVENTION

The object of the invention is to facilitate the identification of interventional instruments and in particular to enable and support automatic identification.

The object is achieved in that an interventional instrument is provided with a marking element which is recognizable in the X-ray image. A marking element in this context is understood to mean not simply any element of the instrument that can somehow be seen only in the X-ray image, but a special X-ray opaque element which is attached to the instrument and serves exclusively for identification of the instrument. The marking elements can identify different instruments such as catheters in different ways so that the latter are easy to distinguish in the X-ray image. An automatic image analysis is also supported in this way. Markings can also be embodied in particular in such a way that they enable the position of the instrument to be determined in the three-dimensional space, indeed also by means of automatic image recognition.

The marking elements can be embodied for example as sphere-shaped or ring-shaped.

Sphere-shaped marking elements have the advantage that a center-of-mass calculation of the sphere is usually possible from the image data. In this way an accuracy in the calculation of the position of the marking elements can be achieved down into the subpixel range (referred to pixels in a detector image).

Ring-shaped marking elements have in particular the advantage that they can allow the instrument to be uniquely identified in the manner of a barcode, which simplifies an automatic analysis of the X-ray image. In particular a plurality of ring-shaped marking elements can be provided adjacent to one another. As in the case of a barcode, the distances between the different ring-shaped marking elements can vary. The standard case is that the spacings of the ring-shaped marking elements are constant over the circumference of the ring-shaped elements, i.e. that the distance is uniform even though it is variable in order of magnitude. In other words the coding can also be implemented via the spacings of the ring-shaped elements. With three elements the spacing between the first and the second marking element may be different from the spacing between the second and the third marking element.

In a further embodiment, however, the spacing of the ring-shaped marking elements does not have to be uniform, but rather the spacing of the ring-shaped marking elements relative to one another can vary over the circumference of the rings. In other words the rings in the instrument can be "lop-sided" with the result that the spacing on one side of the instrument is greater than on the other side.

The ring-shaped marking elements can also be of different thickness compared to one another. In this case, too, a directional orientation can be provided in that the thickness varies over the circumference of the rings, i.e. that the rings on one side of the catheter are thicker than on the other side.

A non-rotationally symmetrical marking element can also be provided, in the form of a lamella for example. A lamella of said kind would be visible as a square or as a bar depending on its rotation about the longitudinal axis. This makes it easier to determine the position of the interventional instrument in the three-dimensional space.

The marking elements usefully consist of metal, lead for example. Two marking elements can also consist of different metals, one of lead and the other of platinum for example. In this way it is possible also to identify the metal as such by recording images at different penetrating powers of the X-ray radiation. In particular, given suitable selection of the penetrating power, the platinum appears more clearly or less clearly in the image, while the lead can tend to appear consistently clearly in the image.

Thus, if an interventional instrument cannot be identified further by the width of the rings, an identification based on the material used can be performed.

Contrast media can also be used as marking elements instead of metals. In this case conventional iodine contrast media, which are typically injected into the blood stream, are used, although these then specifically do not leave the catheter but are contained in the catheter in a closed tube. The contrast medium is of course effective irrespective of whether it is present directly in the blood or indirectly in a tube, with the result that the instrument (the catheter) appears strongly highlighted in the image on account of the contrast medium, it being possible to determine the course of the catheter easily over a certain length owing to the shape of the tube. The individual interventional instruments can be differentiated and identified in the image in each case according to the shape and length of the tubes.

In a preferred embodiment, a marking element, for example a sphere-shaped marking element, is provided at the instrument tip, and at least one further element is provided on the instrument behind the instrument tip. The ring-shaped metallic marking elements or else S-shaped metallic marking elements can be used in this case. The marking element at the instrument tip serves to identify the position of the instrument, while the elements on the instrument behind the instrument tip serve for recognizing the instrument in the image.

BRIEF DESCRIPTION OF THE DRAWINGS

Preferred embodiments will now be described with reference to the drawings, in which:

FIG. 1 shows an inventive interventional instrument (an inventive catheter according to a first embodiment, FIG. 2 shows an inventive catheter according to a second embodiment, and FIG. 3 shows an inventive catheter according to a third embodiment, FIG. 4 shows two catheters, and how they can be distinguished from each other in an X-ray image on the basis of marking elements, FIG. 5 shows a variation of an inventive catheter having marking elements made of two different metals with representation using suitably chosen hard radiation, and FIG. 6 shows the catheter from FIG. 5 with representation using suitably chosen soft radiation, FIG. 7 shows an inventive catheter, seen from its right-hand side in the image, FIG. 8 shows the catheter from FIG. 7 seen vertically, FIG. 9 shows the catheter from FIG. 7, seen from its left-hand side, FIG. 10 shows a sphere-shaped marking element in an X-ray image with pixel grid, and FIG. 11 shows the image from FIG. 10 in pixeled form.

DETAILED DESCRIPTION OF THE INVENTION

Figure 5:
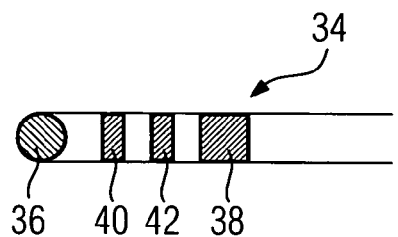

FIG. 1 shows a section of a catheter 10, specifically the tip 12 of the catheter and the following section of the catheter. A sphere-shaped marking element 14 is located at the tip of the catheter 12. Behind the catheter tip there are further marking elements, namely ring-shaped marking elements 16, 18 and 20. In this case the ring-shaped marking elements 16 and 18 are narrower than the ring-shaped marking element 20. Overall, the ring-shaped marking elements can identify the catheter 10 in the manner of a barcode.

In an embodiment variant which is shown in FIG. 2, a serpentine, i.e. S-shaped, marking element 22 is linked to the sphere-shaped marking element 14.

In an embodiment according to FIG. 3, the catheter 10 has a jacket tube 24 which contains a fluid, namely an iodine contrast medium.

A common feature of the embodiments according to FIG. 1 is that the marking elements are recognizable in the X-ray image, whereas the actual catheter is essentially not to be seen in the X-ray image. Since the electrodes which are conventionally disposed on the catheter and are required for the actual electrophysiological examination may also be visible in the X-ray image (because they are made of metal), said electrodes can be incorporated in the identification of the catheter; for example acting in combination with the marking elements (not shown in the figure).

The characteristic shape of the markings permits a unique identification of the catheters. This is shown in FIG. 4. Here can be seen the catheter 28 which, in a similar manner to the catheter 10 from FIG. 1, has a sphere-shaped tip 14, two narrow rings 16, 18 and a somewhat wider ring 20. Also shown is the catheter 26, which has a sphere-shaped tip 14, a somewhat wider ring 30 and a somewhat narrower ring 32. The two catheters 26 and 28 can be distinguished from each other by the arrangement of the rings 30 and 32 on the one hand and 16, 18 and 20 on the other. Even if only the sphere-shaped marking elements 14 and the rings are all that can be seen of the catheters in the X-ray image, the catheters can be clearly separated from each other. Accordingly, the electrophysiologist who introduces the catheters does not have to continuously track the catheters further, but can introduce the catheters into the patient without reference to the X-ray image and recognize the catheters on the X-ray image again later. In particular automatic image recognition and identification of the two catheters 26 and 28 is also possible.

An embodiment variant is shown in FIG. 5. FIG. 5 shows a catheter 34 which has two marking elements 36 and 38 made of lead and two marking elements 40 and 42 made of platinum.

The two different materials, lead and platinum, have different absorption behaviors. The absorption behavior when the acceleration voltage of an X-ray tube is varied is essentially determined by the K edges of the absorption materials used. This is around 78 kV for platinum, whereas it is around 88 kV for lead. If this limit value is exceeded, the absorption increases sharply, thus making the image darker. Special X-ray filters can in fact be used which make the spectrum monochromatic to a limited degree. Through appropriate choice of said filters it is possible to exploit the effect of a different absorption of X-ray radiation by platinum and lead. For example, on the one hand a narrow, tight spectrum at 60 kV can be used and on the other hand a spectrum at 83 kV. With the second spectrum, as will be shown below with reference to FIG. 5, the absorption of the marking element made of platinum increases compared to the marking element made of lead. In the following reference will be made to appropriate hard and appropriate soft radiation, by which the filtering and the suitable choice of the acceleration voltage at the X-ray tube are meant.

In the situation indicated in FIG. 5, in which an X-ray image has been taken using appropriate hard radiation, the different marking elements 36, 38, 40 and 42 appear roughly equally well-defined in the image.

Figure 6:
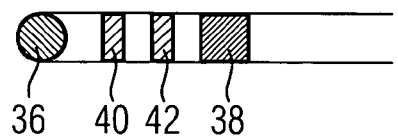

FIG. 6 shows the situation in which an X-ray image has been taken using appropriate soft X-ray radiation. In this case the platinum elements 40 and 42 can be recognized much less clearly in the image than the lead marking elements 36 and 38. The use of different metals for the marking elements therefore allows a further means of identifying the catheters. If examining the shape of the marking elements in the image is not sufficient for differentiating the catheters, the use of different materials can help in improving the recognizability of the various catheters.

Figure 7:
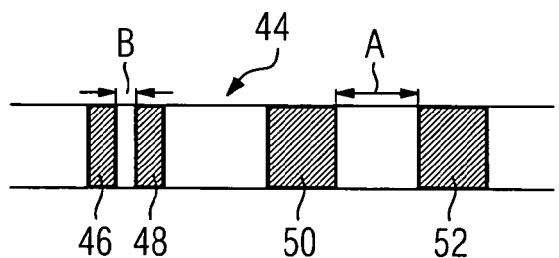
Figure 8:
Figure 9:
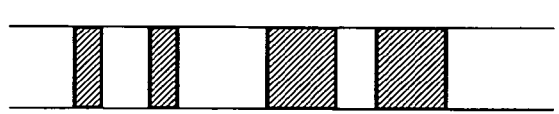

FIGS. 7 to 9 show an embodiment of a catheter 44 in which ring-shaped marking elements are also used. FIG. 7 shows the catheter 44 viewed from the right-hand side of the catheter, FIG. 8 from above and FIG. 9 from the left-hand side of the catheter. The catheter has two narrow rings 46, 48 and two wider rings 50, 52. The observed spacings between the rings 46, 48 on the one hand (distance B) and between the rings 50, 52 on the other hand (distance A) are important. If the catheter is tilted from the right side to the left side, the observed distance B between the rings 46 and 48 increases. If the catheter is tilted from the right side to the left side, the observed distance A between the rings 50 and 52 is reduced.

The embodiment according to FIGS. 7 to 9 also enables the directional orientation of the catheter to be recognized in the X-ray image. This is also possible with automatic image analysis. This facilitates the recognition of how the catheter is positioned three-dimensionally in the body of the patient, which is to say that additional information can be obtained. The three-dimensional information makes it easier for the electrophysiologist in particular to place the catheter in the body of the patient.

The rings can therefore be used as shown in a variety of ways for identifying a catheter, namely by a different sequence of rings of different widths (FIG. 4), through use of different materials for the rings (FIGS. 5 and 6) and by changing the spacing of the rings along the circumference of the same (FIGS. 7 to 9).

The variation in the spacings of rings shown with reference to FIGS. 7 to 9 does not necessarily result from a change in the spacing of the rings along the circumference of the same. Even if the spacing is kept constant over the circumference, different spacings of the rings can be detected in different X-ray images. This is dependent on the spatial orientation of the catheter in space, i.e. whether the catheter is located higher up or lower down, and where. A careful and precise analysis of the spacings of the rings on a catheter can therefore yield information relating to its spatial orientation in any case.

Figure 10:
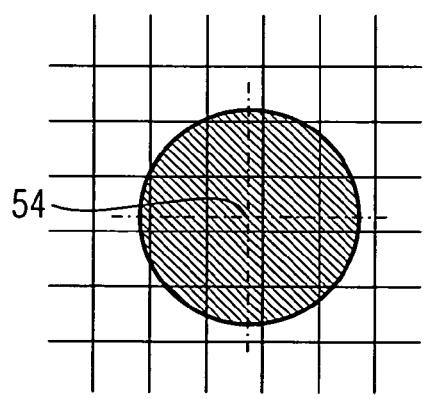
Figure 11:
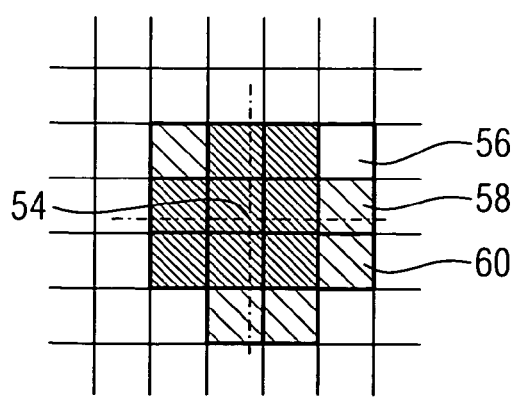

The sphere-shaped marking elements can be used in particular for locating a coordinate. The center of mass of a sphere is particularly easy to determine in the pixel image. FIG. 10 shows a sphere with a pixel grid superimposed thereon, the center of mass of the sphere being marked by a cross and identified by the reference numeral 54. FIG. 11 shows an X-ray image as taken of the sphere, i.e. the illustration from FIG. 10 in pixeled form. Although the sphere shape can now only be guessed at with reference to FIG. 11, it is nonetheless still possible to determine the center of mass as before on the basis of the pixels. The brightness values that are assigned to the individual pixels 56, 58 and 60 are indicated here by different shadings. A pixel 58 in which only half the sphere lies has a lower gray shading than a pixel 60 in which all of the sphere lies or a higher gray shading than a pixel 56 in which the sphere lies only peripherally. The center of mass 54 can be determined by suitable weighting on the basis of the gray shadings.

It is therefore not only the ring-shaped marking elements that are useful, but also at least one sphere-shaped marking element, whereby it can be seen in FIG. 1 that in particular the tip 12 can be marked by the sphere-shaped marking element 14.

It should be pointed out that with the exception of the marking elements the catheters can be fabricated as is necessary for their customary function. In particular details of the catheter tip for other purposes than for those of marking cannot be reflected in the illustration within the scope of the present invention, which does not however mean that the marking elements are intended to restrict the design of the catheter in any shape or form.

The invention claimed is:

1. A system for determining an orientation of an interventional instrument within a body when the interventional instrument is used for a medical procedure, comprising:
   an interventional instrument comprising an instrument specific opaque marking element comprising a sphere-shaped element and at least one ring-shaped element, and which is recognized in an x-ray image for identifying the instrument, wherein the at least one ring-shaped element has a different orientation when viewed from a left side of the instrument, from above the instrument, and from a right side of the instrument, so that a directional tilt of the instrument is recognized based on the orientation viewed;
   a pixel grid configured to be superimposed over an x-ray image of the sphere-shaped element to determine a center of mass of the sphere-shaped element based on an amount of shading of pixels of the sphere-shaped element in the x-ray image with the pixel grid superimposed over the sphere-shaped element;
   wherein the opaque marking element is comprised of a material so that the opaque marking element is visible in the x-ray image while other parts of the interventional instrument are not distinguishable in the x-ray image so that the sphere-shaped element is configured for locating a coordinate system by determining a center of mass based on a shading of pixels on the sphere-shaped element in the x-ray image by superimposing the pixel grid over the sphere-shaped element to identify the center of mass.

2. The instrument as claimed in claim 1, wherein the at least one ring-shaped element is a plurality of ring-shaped marking elements, with different distances between the plurality of ring-shaped marking elements when the instrument is viewed from the left side, the right side, and the top side.

3. The instrument as claimed in claim 2, wherein the plurality of ring-shaped marking elements comprises at least three adjacent ring-shaped elements with which a spacing between the first and the second ring-shaped marking elements is different from a spacing between the second and the third ring-shaped marking elements.

4. The instrument as claimed in claim 2, wherein the plurality of ring-shaped marking elements have a plurality of different thicknesses.

5. The instrument as claimed in claim 1, wherein the marking element is made of a metal.

6. The instrument as claimed in claim 5, wherein the marking element is made of a plurality of different metals.

7. The instrument as claimed in claim 6, wherein the metals are lead and platinum.

8. The instrument as claimed in claim 1, wherein the marking element is an x-ray contrast medium in a closed sheath.

9. The instrument as claimed in claim 1, wherein the sphere-shaped element is at a tip of the instrument and the at least one ring-shaped element is on the instrument behind the tip.

10. The instrument as claimed in claim 9, wherein the the at least one ring-shaped element is different from the sphere-shaped element.

11. The instrument as claimed in claim 1, wherein the instrument is a catheter.

12. The instrument as claimed in claim 1, wherein the instrument is automatically identified by an electronic device.

13. The instrument as claimed in claim 1, further comprising at least one S-shaped marking element linked to the at least one marking element which is sphere-shaped.

14. The instrument as claimed in claim 1, further comprising a jacket tube around an outer surface of the interventional instrument which contains a fluid.

* * * * *